United States Patent
Waanders et al.

(10) Patent No.: US 6,803,436 B2
(45) Date of Patent: Oct. 12, 2004

(54) TRANSPORTABLE AND SAFELY PACKAGED ORGANIC PEROXIDE FORMULATIONS COMPRISING REACTIVE PHLEGMATISERS

(75) Inventors: Petrus Paulus Waanders, Goor (NL); Bart Fischer, Leusden (NL); Johannes Isodorus Roes, Epse (NL)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 10/026,418

(22) Filed: Dec. 19, 2001

(65) Prior Publication Data

US 2002/0091214 A1 Jul. 11, 2002

Related U.S. Application Data

(60) Provisional application No. 60/257,486, filed on Dec. 22, 2000.

(30) Foreign Application Priority Data

Feb. 5, 2001 (EP) .............................................. 01200427

(51) Int. Cl.$^7$ ................................................. C08F 4/38
(52) U.S. Cl. .................... 526/230.5; 526/227; 526/228; 526/232.3; 526/347; 526/348.2; 526/348.3; 526/348.5; 568/559; 502/160; 525/387; 525/938; 252/182.18; 252/182.23; 422/1
(58) Field of Search ............................. 526/230.5, 347, 526/348.2, 348.3, 348.5, 227, 228, 232.3; 252/182.13, 182.23, 182.18; 422/1; 525/387, 938; 568/559; 502/160

(56) References Cited

U.S. PATENT DOCUMENTS

| | | | | |
|---|---|---|---|---|
| 3,591,540 A | * | 7/1971 | Praskach | 568/559 |
| 4,029,875 A | | 6/1977 | Gloriod et al. | 526/308 |
| 4,131,728 A | | 12/1978 | Priddy | 526/204 |
| 4,178,263 A | | 12/1979 | Priddy | 252/186 |
| 4,499,244 A | * | 2/1985 | Honsberg | 525/384 |
| 5,347,055 A | * | 9/1994 | Priddy et al. | 568/559 |
| 5,808,110 A | | 9/1998 | Torenbeek et al. | 549/352 |

FOREIGN PATENT DOCUMENTS

| | | | | |
|---|---|---|---|---|
| WO | WO 93/25615 | 12/1993 | | C08K/5/14 |
| WO | WO 96/03397 | 2/1996 | | C07D/323/00 |

OTHER PUBLICATIONS

Alexandrov, Yu.A., et al., "Reactions of Organoelement Peroxides of the Silicon Subgroup with Olefins," Journal of Organometallic Chemistry 157 (1978), p.p. 267–274.

* cited by examiner

Primary Examiner—Fred Teskin
(74) Attorney, Agent, or Firm—Richard P. Fennelly

(57) ABSTRACT

The invention relates to a method to safely produce, handle and transport packaged organic peroxide formulations comprising a reactive phlegmatiser and to the use of such packaged material in polymerisation and polymer modification processes, particularly the high-pressure (co) polymerisation process of ethylene and/or the suspension (co)polymerisation process of styrene.

13 Claims, No Drawings

TRANSPORTABLE AND SAFELY PACKAGED ORGANIC PEROXIDE FORMULATIONS COMPRISING REACTIVE PHLEGMATISERS

The present application claims priority from European Patent Application No. 01200427.1, filed on Feb. 5, 2001 and from U.S. Provisional Application Ser. No. 60/257,486, filed Dec. 22, 2000.

The invention relates to containers containing specific organic peroxide formulations that can be handled, produced, and shipped in a safe manner and where the organic peroxide formulations contained therein can be used in polymerisation processes where the resulting polymer has a reduced level of undesired residues of low-molecular weight and/or inert phlegmatising agents.

Organic peroxides have long been known. Due to the safety hazards associated with most of them, they are often diluted with one or more specific solvents, also known as phlegmatisers. Classical phlegmatising agents are hydrocarbons and esters, such as phthalates.

U.S. Pat. No. 4,131,728 discloses a polymerisation process employing shock-sensitive peroxides in improved phlegmatisers. The improved phlegmatisers are specific monomers that do not homopolymerise. Exemplified suitable phlegmatising monomers are maleic and citraconic anhydride and esters thereof, fumarates and fumaronitriles, cinnamates and cinnamonitriles, and stilbene.

U.S. Pat. No. 4,029,875 discloses an ethylene polymerisation process employing a mixture of organic peroxides and cyclic olefins, styrene, or styrene homologues bearing alkyl substituents on the benzene nucleus to reduce the consumption of initiator in the process and to improve the optical and mechanical properties of the polyethylene produced.

Yu. A. Alexandrov et al. disclose in *Journal of Organometallic Chemistry*, 157 (1978), 267–274, that silicon subgroup organoelement peroxides (peroxides where one Si, Ge or Sn atom is attached to the peroxygen function) in model studies showed specific decomposition behaviour and that the ratio of proton abstraction and addition to double bonds varies depending on the olefin that is used as the solvent. The present invention does not relate to silicon subgroup organoelement peroxides.

In WO 96/03397, disclosing particular safe cyclic ketone formulations, a variety of potential phlegmatisers is mentioned. However, ketone peroxides, including cyclic ketone peroxides, are not the subject of the present invention. It is noted that Akzo Nobel markets formulations of tert butyl peroxymaleate in dibutylmaleate solvent for specific use in unsaturated polyester resin curing processes with specific curing profiles.

Although many phlegmatisers are known and although reactive compounds have been combined with certain organic peroxides before, there is a need in the industry for packaged peroxide formulations that can be produced, handled, and shipped in a safe manner and where the peroxide formulations, when used in polymerisation reactions, do not lead to the presence of undesired phlegmatising agent in the resin that is produced. The most pressing need is for the supply of peroxides for use in the styrenics and high-pressure ethylene (co)polymerisation industry, where the phlegmatising agent as such should not end up in the final resin. However, such improved formulations which would reduce the amount of low-molecular weight (<1,000 Dalton) products, especially solvents, in the final product could be beneficial also in the process of making acrylic resins, to modify polymers, e.g. polypropylene, and to cure or cross-link polymers, such as polyethylene and unsaturated polyester resins.

In the styrenics industry it is preferred, especially when expandable polystyrene is produced using a suspension polymerisation process, that the phlegmatiser is apolar in nature to prevent the final resin from becoming more hydrophilic, which interferes with the foaming process. Due to the nature of the polymerisation process, relatively small quantities of concentrated, preferably technically pure, peroxide formulations are used. Traditionally, containers shipped for use in this industry are less than 500 liters, preferably less than 250 liters, more preferably less than 30 liters in size. For economic reasons and to reduce the amount of packaging material, the container will preferably contain more than 1 liter, more preferably more than 2 liters, most preferably more than 10 liters of the (phlegmatised) peroxide, such as the Nourytainers® ex Akzo Nobel. There is a need for a "drop in" replacement for the existing products, so that polymerisation recipes need not be changed, which leads to an improved product (containing less low-molecular weight compounds). However, there is also a need for more dilute peroxide formulations, which, for example, could be dosed automatically and/or stored safely in large-size (200 liters, preferably 500 liters or more) storage tanks.

In the high-pressure ethylene (co)polymerisation process, typically very dilute peroxide formulations, often containing just 10–40% w/w of peroxide and 60–90% w/w of phlegmatiser, are supplied. Particularly in these processes it is highly desirable that most if not all of the phlegmatiser be consumed or reacted, so that the resulting polymer contains an acceptably low amount of phlegmatiser. It is noted that because quite dilute peroxide formulations are to be supplied, it is preferred that the safety characteristics of the formulations are such that the container in which the peroxide formulations are shipped is at least 200 liters, preferably at least 1,000 liters, most preferably more than 10,000 liters in size.

Furthermore, there is a prejudice against shipping and storing large containers which contain peroxides in combination with reactive compounds for fear of increasing the hazards associated with the handling of said organic peroxides. More particularly, containers containing a peroxide will show a run-away thermal decomposition, also known as a thermal explosion, whenever the heat developing in the container due to decomposition of the peroxide is higher than the heat transmitted to the surroundings. The larger a (practical) container, the lower the surface to volume ratio will be. Therefore, shipment in larger containers is more hazardous. The presence of reactive compounds in peroxide formulations has always been expected to result in a less safe product, because the heat of reaction will contribute to the heat being generated, while the heat transfer to the surroundings is not increased. Hence, the shipment of peroxides dissolved in reactive compounds has never been commercialised, except for some peroxydicarbonates which have been shipped in monomers with allylic unsaturated groups which do not readily polymerise and must be shipped at very low and impractical temperature of −20° C., or in monomers that do not homopolymerise at all (meaning that no more than 1% of the monomer is converted in a test where a 1:1 weight ratio mixture of monomer and peroxide is kept at 40° C. for a period of 100 hours).

Surprisingly, we have found that containers with a size of more than 1 liter and containing organic peroxides and reactive diluents can nevertheless be shipped in a safe fashion at temperatures above −20° C., preferably above −10° C., more preferably above 0° C. The use of the reactive diluent gives the benefit of reduced unbound phlegmatiser in the polymer (so that the polymer contains less volatile product). Particularly in a high-pressure ethylene (co) polymerisation process, the phlegmatiser is consumed without the properties of the polymer being changed and without the polymerisation process being adversely affected. The reduced unbound phlegmatiser levels improve the organoleptic properties of the resulting (co)polymer and may even obviate a vacuum treatment of the molten polymer to reduce volatile material.

Accordingly, we claim a method to safely transport specific peroxide formulations comprising reactive phlegmatisers, containers comprising such specific peroxide formulations that are safely transportable, some preferred peroxide formulations that can be transported/shipped in such a fashion, and the use of the preferred peroxide formulations in polymerisation processes, particularly the (co)polymerisation process of ethylene at high pressure to make so-called (modified) low density polyethylene (LDPE) and the suspension polymerisation process to make expandable polystyrene. However, as said, the peroxide formulations according to the invention may be equally desirable in other conventional radical polymerisation, curing, and/or modification processes.

More specifically, we claim a method to safely transport peroxide formulations in containers having a size greater than 1 liter, characterised in that the containers are filled with:

1. from 90 to 1 percent by weight, based on the weight of the content of the container, (% w/w) of one or more peroxides selected from the group consisting of peroxyesters, including peroxyesters of ketone peroxides, peroxycarbonates, including peroxycarbonate derivatives of ketone peroxides, diacylperoxides with from 1 to 48 carbon atoms, diperoxyketals, trioxepans, dialkylperoxides, mixed peroxides, and mixtures of any two or more of these peroxides,
2. from 10 to 99% w/w of one or more phlegmatisers of which the sole phlegmatiser or, if more than one phlegmatiser is used, the mixture of phlegmatisers has a flash point greater than 5° C. and a boiling point that is more than 60° C. higher than the self-accelerating decomposition temperature (SADT) of the peroxide formulation, and the phlegmatiser is selected from the group of compounds that react effectively in the polymerisation process.

The flash point is determined in accordance with method ISO 3679 using a Setaflash tester (model 1374 and a sample of 2 ml for flash points up to 110° C. and/or a model 1377 and a sample of 4 ml for flash points from 110–300° C.). The boiling point is determined in accordance with EU Council Directive 92/69/EEC of Jul. 31, 1993 (17th adaptation of Council Directive 67/548/EEC) using a Mettler TA-4000 DSC at a temperature scanning rate of 5° C./min using a sample cup with a lid with a pin hole of about 0.5 mm. The experiments were carried out in duplicate. The boiling point is the average of the onset temperatures as determined by intersecting the base line and the extrapolated line touching most of the shoulder of the front of the endotherm peak. Preferably, the boiling point of the reactive phlegmatiser is above 60° C. The SADT is determined a conventional way, using a Differential Scanning Calorimeter (DSC) that is heated at a rate of 2° C. per minute. The sample size is about 60 mg, the cups that are used of the type ME HP stainless steel, 270 µl. The SADT is defined to be the temperature that is 50° C. below the temperature where the total heat developed is 100 W per kg of sample.

Preferably, the containers are more than 200 liters, more preferably more than 1,000 liters, most preferably more than 10,000 liters in size. Preferably, they contain 80-2% w/w of peroxide, more preferably 75-5% w/w, and most preferably 50-10% w/w of peroxide. The higher concentrations (>40% w/w) are preferred when small containers are used (holding less than 200 liters, preferably less than 50 liters, of product), while the lower concentrations (<40% w/w) are preferred when the formulations are shipped in larger containers holding 200 liters or more of the peroxide formulation.

A preferred group of peroxides for shipment in accordance with the present invention are peroxides comprising one or more of the following moieties; peroxyester of the formula —C(O)OO—, peroxycarbonate of the formula —OC(O)—, diacylperoxide of the formula —C(O)OOC(O)—, dialkylperoxide of the formula —OO—, and trioxepan as disclosed in European Patent Application No. 00203888.3, so that peroxides of this group include mixed peroxides (containing any two different peroxygen-bearing moieties in one molecule), and mixtures of any two or more of these peroxides. It is noted that If the peroxides are not liquid at room temperature, they may be soluble in the phlegmatiser or mixture of phlegmatisers. Although the peroxides can be oligomeric or polymeric in nature, it is preferred that they are of the conventional type comprising one, two or three peroxygen bonds in the molecule. Most preferred are (di)peroxyesters, such as 1,1,4,4-tetramethylbutyl-1,4-di(peroxy-2-methylpropanoate), tert-butylperoxy neodecanoate, tert-amylperoxy neodecanoate, 1,1,3,3-tetramethyl butyl-1-peroxy neodecanoate, 1,1-dimethyl-3-hydroxy butyl-1-peroxy neodecanoate, tert-butylperoxy pivalate, tert-amylperoxy pivalate, 1,1,3,3-tetramethyl butyl-1-peroxy pivalate, 1,1-dimethyl-3-hydroxy butyl-1-peroxy pivalate, tert-butylperoxy 2-ethylhexanoate, tert-amylperoxy 2-ethylhexanoate, 1,1,3,3-tetramethyl butyl-1-peroxy 2-ethylhexanoate, 1,1-dimethyl-3-hydroxy butyl-1-peroxy 2-ethylhexanoate, tert-butylperoxy benzoate, tert-amylperoxy benzoate, 1,1,3,3-tetramethyl butyl-1-peroxy benzoate, 1,1-dimethyl-3-hydroxy butyl-1-peroxy benzoate, tert-butylperoxy 3,3,5-trimethylhexanoate, tert-amylperoxy 3,3,5-trimethylhexanoate, 1,1,3,3-tetramethyl butyl-1-peroxy 3,3,5-trimethylhexanoate, 1,1-dimethyl-3-hydroxy butyl-1-peroxy 3,3,5-trimethylhexanoate, tert-butylperoxy isobutyrate, tert-amylperoxy isobutyrate, 1,1,3,3-tetramethyl butyl-1-peroxy isobutyrate, and 1,1-dimethyl-3-hydroxy butyl-1-peroxy isobutyrate, dialkylperoxides, such as di-tert-butyl peroxide, tert-butyl tert-amyl peroxide, and di-tert-amyl peroxide, and diacyl peroxides, such as bis(3,3,5-trimethylhexanoyl) peroxide. Preferably, the peroxides according to the invention are not shock-sensitive.

The reactive phlegmatiser used in accordance with the present invention must react efficiently in the polymerisation process employing the peroxide formulation. The term "react efficiently" as used herein means that at least 25%, preferably at least 50%, and most preferably more than 75% by weight of the reactive phlegmatiser is reacted in the polymerisation process. In other words, in the most preferred situation, less than 25% by weight of the phlegmatiser used in the process is extractable from the resin (without destruction of the resin). Reaction conditions vary widely; take, for example, the differences between a suspension polymerisation process of styrene, where the bulk of the monomer is typically reacted at temperatures of up to about 100° C. at about atmospheric pressure (1 bara), and high-pressure ethylene polymerisation processes, which are conducted at temperatures up to 400° C. and pressures up to 3,500 bara. The skilled person knows that the reactivity of the phlegmatiser used according to the invention depends on the reaction conditions, such as temperature, pressure, radical concentration, monomer concentration, and the type of monomer. However, whether or not it is a reactive phlegmatiser is easily tested by checking the amount of unreacted phlegmatiser in the polymer. It is to be understood that the term "reactive phlegmatiser" does not relate to conventional phlegmatisers, which do not react and often plasticise the resulting resin.

It is essential that the reactive phlegmatiser fulfill the flash and boiling point requirements. If it does not, then it is less preferred and it can only be used together with one or more other reactive or conventional phlegmatisers such that the mixture does fulfill the flash and boiling point requirements.

It is furthermore to be noted that the reactive phlegmatizers do not encompass regular monomers as used in radical homopolymerization processes, such as styrene and methylmethacrylate. A convenient way to discriminate between suitable reactive phlegmatizers according to the invention and undesired phlegmatizer/solvents, is to determine the SADT of a 50/50 blend, on a weight basis, of a peroxide and a known inert phlegmatizer, such as octane or isododecane, and the SADT of a 50/50 blend of the same peroxide and the reactive phlegmatizer. If the SADT is lowered by 5° C. or more, the phlegmatizer is not a reactive phlegmatizer according to the invention. Preferably, the SADT is not lowered at all, or even increased.

Preferred reactive phlegmatisers are α-methyl styrene, (α-methyl) o-methyl styrene, (α-methyl) m-methyl styrene, (α-methyl) p-methyl styrene, stilbene, (cyclic) olefins, unsaturated esters, unsaturated ethers, unsaturated carboxylic acids (and anhydrides thereof), aldehydes, ketones, alcohols, and mixtures thereof. More preferred reactive phlegmatisers are α-methyl styrene, (α-methyl) o-methyl styrene, (α-methyl) m-methyl styrene, (α-methyl) p-methyl styrene, itaconate esters, citraconate esters, (cyclic) olefins, aldehydes, ketones, alcohols, and mixtures thereof. Even more preferred reactive phlegmatisers are α-methyl styrene, (α-methyl) o-methyl styrene, (α-methyl) m-methyl styrene, (α-methyl) p-methyl styrene, (cyclic) olefins, aldehydes, ketones, alcohols, and mixtures thereof. Most preferred is the use of (α-methyl styrene and/or (cyclic) olefins.

Preferred (cyclic) olefins are selected from the group consisting of cyclopentene, cyclohexene, cycloheptene, cyclooctene, α-pinene, olefins, such as any isomer selected from the group consisting of hexene, heptene, octene, nonene, decene, undecene, and dodecene, especially α-olefins, such as 1-hexene, 1-heptene, 1-octene, 1-nonene, 1-decene, 1-undecene, and 1-dodecene, and mixtures of any two or more of these (cyclic) olefins. It is noted that the alkenes can be present in any isomeric form, hence they can be linear or branched, and the unsaturated bond can be anywhere in the molecule and both cis and trans configurations are acceptable. Also the olefin can have more than one unsaturated bond in the molecule as in alkadienes (diolefins). If the alkene is branched, the branching preferably is not on the carbon atom attached to a double bond. In other words, the alkene preferably is of the structure $R^1R^2R^3CH\!=\!CH\!-\!CR^4R^5R^6$ (formula I), wherein each of $R^{1-6}$ represent, independently, hydrogen or a hydrocarbon moiety with preferably up to 12 carbon atoms. More preferably, R is non-aromatic, to prevent environmental problems. The use of 1-alkenes according to formula I is most preferred.

The formulations can be produced by blending one or more pure peroxides with one or more of the reactive phlegmatisers. Alternatively, one or more peroxides containing conventional diluents/phlegmatisers can be blended with one or more of the reactive phlegmatisers. Also, it is possible to produce the peroxide in a medium comprising one or more of the reactive phlegmatisers and, optionally, conventional phlegmatiser, such that the packaged end product of the peroxide synthesis step, optionally after one or more other process steps, e.g. a washing step, is a packed peroxide formulation according to the invention. Preferably, the final formulation is essentially free of chlorinated species, since such species may lead to corrosion problems or interfere with the polymerisation process in which the formulations are used as a source of free radicals.

Conventional phlegmatisers include, but are not limited to the group consisting of hydrocarbons, such as (diesel) fuel, paraffinic and white oils, oxygenated hydrocarbons, such as ethers, epoxides, and esters. Examples of preferred conventional phlegmatisers are hydrocarbon solvents, including isododecane, toluene, xylene, (diesel) fuel, paraffinic oils, and white oils, esters, such as phthalates and adipates, ethers, and epoxides, such as epoxidised soybean oil.

Preferably, the peroxide formulations according to the invention comprise: 75-1 percent by weight, based on the weight of the formulation, (% w/w) of one or more of the organic peroxides, 25–99% w/w of one or more reactive phlegmatisers, and 0–50% w/w of one or more conventional phlegmatisers (that are not α-olefin), up to a total of 100% w/w.

The polymerisation processes for which the peroxide (initiator) formulations according to the invention are pre-eminently suited are of the conventional type, and include processes to make poly vinyl chloride, copolymers of vinyl chloride, poly(meth)acrylate (co)polymers, etc. Preferably, the process is a styrene suspension (co)polymerisation or a high-pressure (co)polymerisation process of ethylene. Comonomers that may be used in the (co)polymerisation process of ethylene are of the conventional type and include alkenes, such as propene, (cyclo)hexene and (cyclo)octene, and vinyl acetate. Comonomers that may be used in the (co)polymerisation process of styrene are of the conventional type and include divinylbenzene. The amount of initiator used in these conventional (co)polymerisation processes will vary, depending on the polymerisation temperature, the capacity for removing the heat of polymerisation, the kind(s) of monomer(s) used, and the applied pressure. Usually, from 0.001–25% w/w of initiator, based on the total weight of the monomers, is employed. Preferably, from 0.001–15% w/w of initiator is employed.

If so desired, the products according to the invention can also be used in the process to modify a (co)polymer, such as in cross-linking, grafting, and controlled degradation processes, e.g. the formation of polypropylene with another molecular weight and/or molecular weight distribution. Also in these processes, the products lead to the formation of less volatile matter in the final product. Less volatiles can be beneficial in, for instance, the automotive area, where volatiles can lead to fogging of windows.

A most preferred embodiment of the invention is the transport of large containers ($\geq$200 liters) containing 75-1% w/w, preferably 50-10% w/w, of one or more organic peroxides selected from the group of tert-butylperoxy neodecanoate, tert-amylperoxy neodecanoate, 1,1,3,3-tetramethyl butyl-1-peroxy neodecanoate, 1,1-dimethyl-3-hydroxy butyl-1-peroxy neodecanoate, tert-butylperoxy pivalate, tert-amylperoxy pivalate, 1,1,3,3-tetramethyl butyl-1-peroxy pivalate, 1,1-dimethyl-3-hydroxy butyl-1-peroxy pivalate, tert-butylperoxy 2-ethylhexanoate, tert-amylperoxy 2-ethylhexanoate, 1,1,3,3-tetramethyl butyl-1-peroxy 2-ethylhexanoate, 1,1-dimethyl-3-hydroxy butyl-1-peroxy 2-ethylhexanoate, tert-butylperoxy benzoate, tert-amylperoxy benzoate, 1,1,3,3-tetramethyl butyl-1-peroxy benzoate, 1,1-dimethyl-3-hydroxy butyl-1-peroxy benzoate, tert-butylperoxy 3,3,5-trimethylhexanoate, tert-amylperoxy 3,3,5-trimethylhexanoate, 1,1,3,3-tetramethyl butyl-1-peroxy 3,3,5-trimethylhexanoate, 1,1-dimethyl-3-hydroxy butyl-1-peroxy 3,3,5-trimethylhexanoate, tert-butylperoxy isobutyrate, tert-amylperoxy isobutyrate, 1,1,3,3-tetramethyl butyl-1-peroxy isobutyrate, 1,1-dimethyl-3-hydroxy butyl-1-peroxy isobutyrate, di-tert-butyl peroxide, tert-butyl tert-amyl peroxide, di-tert-amyl peroxide, bis(3,3,5-trimethylhexanoyl) peroxide, 25–99% w/w of one or more reactive phlegmatisers, preferably selected from (cyclo) olefins, most preferably 1-octene, and 0–50% w/w of one or more conventional phlegmatisers, up to a total of 100% w/w.

Since the thus transportable peroxide formulations are pre-eminently suited for use in high-pressure ethylene polymerisation processes, a further preferred embodiment of the invention is the method to (co)polymerise ethylene in a conventional high-pressure radical polymerisation process in which peroxides are produced at another site (i.e. off-site), formulated with a reactive phlegmatiser, safely transported to the polymerisation site, and used in the polymerisation process.

Another most preferred embodiment of the invention relates to the transport of containers containing 75-1% w/w of 1,1,4,4-tetramethylbutyl-1,4-di(peroxy-2-methylpropanoate), 25–99% w/w of one or more reactive phlegmatisers, preferably α-methyl styrene, and 0–50% w/w of one or more conventional phlegmatisers, up to a total of 100% w/w.

Since the thus transportable peroxide formulations are pre-eminently suited for use in styrene suspension polymerisation processes, a further preferred embodiment of the invention is the method to (co)polymerise styrene in a conventional suspension polymerisation process in which peroxides are produced at another site (i.e. off-site), formulated with a reactive phlegmatiser, safely transported to the polymerisation site, and used in the polymerisation process.

The invention is elucidated by the following examples.

EXAMPLE 1 and COMPARATIVE EXAMPLE A

In Example 1, tert-butylperoxy 2-ethylhexanoate (Trigonox 21® ex Akzo Nobel) was diluted with 1-octene (ex Acros Organics, product 12944-0000) in a ratio of 1:1 on a weight basis.

The experiment was repeated in Comparative Example A using n-octane (ex Haltermann GmbH, No. F122900) instead of 1-octene.

Both formulations have about equal safety characteristics, which is expected to allow their shipment in 1,000-liter containers. More particularly, both formulations have a SADT of 40° C. It is noted that a similar tert-butylperoxy 2-ethylhexanoate dilution with styrene resulted in a formulation that is outside the scope of the present invention with a SADT of 30° C. The use of the formulation of Example 1, compared to the use of the product of Comparative Example A, in a high-pressure (co)polymerisation process is expected to result in a much reduced amount of volatile matter in the resulting (modified) LDPE.

EXAMPLE 2 and COMPARATIVE EXAMPLE B 1,1,4,4-Tetramethylbutyl-1,4-di(peroxy-2-methylpropanoate) was produced in a conventional manner by reacting 1,1,4,4-tetramethylbutyl-1,4-dihydroperoxide with isobutanoyl chloride. In Example 2 α-methyl styrene was used as a phlegmatiser already during the process, in an amount such that 50% by weight of 1,1,4,4-tetramethylbutyl-1,4-di(peroxy-2-methylpropanoate) ($CH_3CH(CH_3)C(O)OOC(CH_3)_2CH_2CH_2C(CH_3)_2O-OC(O)CH(CH_3)CH_3$) in α-methyl styrene was packaged after a conventional optional washing step. In Comparative Example B isododecane was used as the phlegmatiser in the same way.

Both products could safely be produced and transported in containers containing 1 liter or more of the formulation at a temperature of 5° C. In both cases the 1-hour half life (measured in a conventional way with DSC using monochlorobenzene as the solvent) of the peroxide was 87° C. When used in a conventional suspension polymerisation process, the contents of the containers of Example 2 are expected to result in polystyrene beads that are essentially free of extractable phlegmatiser, while the use of the contents of the containers of Comparative Example 2 is known to result in polymers from which virtually all isododecane can be extracted.

What is claimed is:

1. A method to safely transport peroxide formulation in containers having a size greater than 1 liter, characterised in that the containers are filled with:

from 90 to 1% w/w of one or more peroxides selected from the group consisting of peroxyestere, peroxycarbonates, diacylperoxides with from 1 to 48 carbon atoms, diperoxyketals, trioxepans, dialkylperoxides, mixed peroxides, and mixtures of any two or more of these peroxides, from 10 to 99% w/w of one or mere phlegmatisers with a joint flash point greater than 5° C. and a joint boiling point that is more than 60° C. higher than the self-accelerating decomposition temperature of the peroxide formulation, said phlegmatiser being selected item the group of compounds that react effectively in a polymerisation process, 0–75% w/w of optional conventional phlegmatisers, up to a total of 100%, with the proviso that it is not a formulation of tert.butyl peroxymaleate with dibutylmaleate.

2. A method to safely peroxide formulation in containers according to claim 1, wherein the peroxyesters are peroxyester derivations of listens peroxides.

3. A method to safely transport peroxide formulation in containers according to claim 1, wherein the peroxycarbonates an peroxycarbonate derivatives of ketone peroxides.

4. A method to produce a polymer by means of a radical polymerisation process wherein at least 25% w/w of the phlegmatiser that was used to phlegmatise the peroxide or peroxides used as a source of free radicals in said process is reacted such that it is not extractable from the polymer by transporting a peroxide formulation-containing container according to claim 1 to the polymerisation unit and introducing its content into the polymerisation process.

5. The method according to claim 4 wherein the polymerisation process is a high-pressure ethylene (co) polymerisation process.

6. The method according to claim 4 wherein the polymerisation process is a suspension styrene (co) polymerisation process.

7. The method according to claim 4 wherein the reactive phlegmatiser is selected tram the group consisting of (cyclic) olefins, aldehydes, ketones, alcohols, and mixtures thereof.

8. The method according to claim 7 wherein the reactive α-olefins are selected from the group consisting of 1-hexene, 1-heptene, 1-octene, 1-nonene, 1-decene, 1-undecene, 1-dodecane, and mixture thereof.

9. The method according to claim 6 wherein the reactive phlegmatiser is α-methyl styrene.

10. A method according to any one of the preceding claims wherein the peroxide is selected from the group consisting of 1,1,4,4-tetramethylbutyl-1,4-di (peroxy-2-methylpropanoate), tert-butylperoxy neodecanoate, tert-amylperoxy neodecanoate, 1,1,3,3-tetramethyl butyl-1-peroxy neodecanoate, 1,1-dimethyl-3-hydroxy butyl-1-peroxy neodecanoate, tert-butylperoxy pivalate, tert-amylperoxy pivalate, 1,1,3,3-tetramethyl butyl-1-peroxy pivalate, 1,1-dimethyl-3-hydroxy butyl-1-peroxy pivalate, tert-butylperoxy 2-ethylhexanoate, tert-amylperoxy 2-ethylhexanoate, 1,1,3,3-tetramethyl butyl-1-peroxy 2-ethylhexanoate, 1,1-dimethyl-3-hydroxy butyl-1-peroxy 2-ethylhexanoate, tert-butylperoxy benzoate, tert-amylperoxy benzoate, 1,1,3,3-tetramethyl butyl-1-peroxy benzoate, 1,1-dimethyl-3-hydroxy butyl-1-peroxy benzoate, tert-butylperoxy 3,3,5-trimethylhexanoate, tert-amylperoxy 3,3,5-trimethylhexanoate, 1,1,3,3-tetramethyl butyl-1-peroxy 3,3,5-trimethylhexanoate, 1,1-dimethyl-3-hydroxy butyl-1-peroxy 3,3,5-trimethylhexanoate, tert-butylperoxy isobutyrate, tert-amylperoxy isobutyrate, 1,1,3,3-tetramethyl butyl-1-peroxy isobutyrate, and 1,1-dimethyl-3-hydroxy butyl-1-peroxy isobutyrate, dialkylperoxides, preferably di-tert-butyl peroxide, tert-butyl tert-amyl peroxide, and di-tert-amyl peroxide, and diacylperoxides.

11. A method according to claim 10, wherein the peroxide is bis(3,3,5-trimethylhexanoyl) peroxide.

12. A polymerization process wherein monomers are polymerized to form a polymer, said process comprising:
   a step wherein a peroxide formulation is transported according the method of claim 1; and
   the polymerization of the monomers is initiated in a subsequent step by the peroxide formulation.

13. A process for the degradation, cross-linking or grafting of a polymer comprising:
   a step wherein a peroxide formulation is transported according the method of claim 1; and
   the degradation, cross-linking or grafting of the polymer in a subsequent step by the peroxide formulation as a source of free radicals.

* * * * *

UNITED STATES PATENT AND TRADEMARK OFFICE
CERTIFICATE OF CORRECTION

PATENT NO.    : 6,803,436 B2
DATED         : October 12, 2004
INVENTOR(S)   : Petrus Paulus Waanders, Bart Fischer and Johannes Isodorus Roes It is certified that error appears in the above-identified patent and that said Letters Patent is hereby corrected as shown below:

Column 8,
Line 27, change "peroxyestere" to -- peroxyesters --
Line 34, change "mere" to -- more --
Line 38, change "item" to -- from --
Line 45, -- transport a -- should appear between "safely" and "peroxide"
Line 47, change "listen" to -- ketone --
Line 48, -- a -- should appear between "transport" and "peroxide"
Line 50, change "an" to -- are --
Line 66, change "tram" to -- from --

Column 9,
Line 4, change "mixture" to -- mixtures --

Signed and Sealed this

Eleventh Day of January, 2005

JON W. DUDAS
*Director of the United States Patent and Trademark Office*